(12) United States Patent
Adams et al.

(10) Patent No.: US 7,628,775 B2
(45) Date of Patent: Dec. 8, 2009

(54) SAFETY Y-PORT ADAPTOR AND MEDICAL CATHETER ASSEMBLY INCLUDING THE SAME

(75) Inventors: Mark L. Adams, Milford, MA (US); Laurence D. Brenner, Northboro, MA (US); Mark DeLegge, Mt. Pleasant, SC (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 358 days.

(21) Appl. No.: 10/950,026

(22) Filed: Sep. 24, 2004

(65) Prior Publication Data

US 2006/0079850 A1    Apr. 13, 2006

(51) Int. Cl.
*A61M 25/00* (2006.01)

(52) U.S. Cl. ...................... 604/284; 604/246

(58) Field of Classification Search ............... 604/284, 604/244–247, 256, 537, 539, 910, 533
See application file for complete search history.

(56) References Cited

U.S. PATENT DOCUMENTS

| | | | |
|---|---|---|---|
| 3,572,375 A * | 3/1971 | Rosenberg .................. 137/512 |
| 4,468,224 A * | 8/1984 | Enzmann et al. ............ 604/247 |
| 4,560,378 A | 12/1985 | Weiland |
| 4,661,110 A | 4/1987 | Fortier et al. |
| 4,666,433 A | 5/1987 | Parks |
| 4,668,225 A | 5/1987 | Russo et al. |
| 4,685,901 A | 8/1987 | Parks |
| 4,701,163 A | 10/1987 | Parks |
| 4,704,111 A | 11/1987 | Moss |
| 4,781,704 A | 11/1988 | Potter |
| 4,842,591 A * | 6/1989 | Luther ........................ 604/537 |
| 4,874,365 A | 10/1989 | Frederick et al. |
| 5,057,093 A | 10/1991 | Clegg et al. |
| 5,071,405 A * | 12/1991 | Piontek et al. ......... 604/103.03 |
| 5,098,378 A | 3/1992 | Piontek et al. |
| 5,098,405 A * | 3/1992 | Peterson et al. ............. 604/247 |
| 5,234,417 A | 8/1993 | Parks et al. |
| 5,242,389 A | 9/1993 | Schrader et al. |
| 5,250,040 A | 10/1993 | Parks et al. |
| 5,290,250 A | 3/1994 | Bommarito |
| 5,306,243 A | 4/1994 | Bonaldo |

(Continued)

FOREIGN PATENT DOCUMENTS

EP    0 497 576 A1    8/1992

*Primary Examiner*—Nicholas D Lucchesi
*Assistant Examiner*—Theodore J Stigell
(74) *Attorney, Agent, or Firm*—Kriegsman & Kriegsman

(57) ABSTRACT

A medical catheter assembly including a safety Y-port adaptor. In one embodiment, the medical catheter assembly is a percutaneous endoscopic gastrostomy (PEG) assembly and includes a PEG tube, the PEG tube having a proximal end, a distal end and a longitudinal conduit. An internal bolster is disposed at the distal end of the PEG tube. The safety Y-port adaptor includes a tubular first arm, a tubular second arm and a tubular third arm, each of the second and third arms being in fluid communication with the first arm. The first arm is coupled to the proximal end of the PEG tube and is fluid communication therewith. A first anti-reflux valve is disposed within the second arm, and a second anti-reflux valve is disposed within the third arm. The anti-reflux valves may be positioned within their respective arms so that each may be biased open by the insertion of a dispensing tip into the arm.

21 Claims, 13 Drawing Sheets

U.S. PATENT DOCUMENTS

| | | | |
|---|---|---|---|
| 5,336,203 A | 8/1994 | Goldhardt et al. | |
| 5,352,215 A | 10/1994 | Thome et al. | |
| 5,399,173 A | 3/1995 | Parks et al. | |
| 5,403,290 A | 4/1995 | Noble | |
| 5,458,583 A | 10/1995 | McNeely et al. | |
| 5,527,280 A | 6/1996 | Goelz | |
| 5,549,657 A | 8/1996 | Stern et al. | |
| 5,591,128 A | 1/1997 | Sithole | |
| 5,749,857 A | 5/1998 | Cuppy | |
| 5,836,924 A | 11/1998 | Kelliher et al. | |
| 5,902,285 A | 5/1999 | Kudsk et al. | |
| 6,019,746 A | 2/2000 | Picha et al. | |
| 6,030,361 A | 2/2000 | Miyashiro | |
| 6,165,168 A * | 12/2000 | Russo | 604/533 |
| 6,464,686 B1 | 10/2002 | O'Hara et al. | |
| 6,582,395 B1 * | 6/2003 | Burkett et al. | 604/96.01 |
| 2003/0009152 A1 | 1/2003 | O'Hara et al. | |
| 2003/0139703 A1 | 7/2003 | Burkett et al. | |
| 2003/0153897 A1 | 8/2003 | Russo | |

* cited by examiner

SAFETY Y-PORT ADAPTOR AND MEDICAL CATHETER ASSEMBLY INCLUDING THE SAME

BACKGROUND OF THE INVENTION

The present invention relates generally to Y-port adaptors of the type suitable for use with medical catheters, such as percutaneous endoscopic gastrostomy (PEG) tubes and percutaneous endoscopic jejunostomy (PEJ) tubes, and relates more particularly to a novel Y-port adaptor of the aforementioned type and to a medical catheter assembly including the same.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. Feeding is then typically performed by administering food through a catheter or feeding tube that has been inserted into the feeding tract, with the distal end of the feeding tube extending into the stomach and being retained therein by an internal anchor or bolster and the proximal end of the feeding tube extending through the abdominal wall.

(For certain patients, it is desirable for food to be administered directly to the patient's jejunum, without first passing through the patient's stomach. In such cases, a jejunostomy is typically performed, a jejunostomy being similar to a gastrostomy, except that a jejunostomy results in the distal end of the feeding tube being implanted in the patient's jejunum, instead of in the patient's stomach.)

Although gastrostomies were first performed surgically, most gastrostomies are now performed using percutaneous endoscopy and result in the implantation of a catheter/bolster assembly (also commonly referred to as a percutaneous endoscopic gastrostomy (PEG) device) in the patient. Two of the more common techniques for implanting a PEG device in a patient are "the push method" (also known as "the Sacks-Vine method") and "the pull method" (also known as "the Gauderer-Ponsky method"). Summaries of the push method and the pull method are provided below; additional information regarding these two methods may be found in the following patents, all of which are incorporated herein by reference: U.S. Pat. No. 5,391,159, inventors Hirsch et al., which issued Feb. 21, 1995; U.S. Pat. No. 5,167,627, inventors Clegg et al., which issued Dec. 1, 1992; U.S. Pat. No. 5,112,310, inventor Grobe, which issued May 12, 1992; U.S. Pat. No. 4,900,306, inventors Quinn et al., which issued Feb. 13, 1990; and U.S. Pat. No. 4,861,334, inventor Nawaz, which issued Aug. 29, 1989.

According to the push method, the distal end of an endoscope is inserted into a patient's mouth and is passed through the esophagus into the stomach. After distension of the stomach by inflation, an entry site on the abdomen is identified, and an incision is made by passing a needle with an outer cannula (e.g., a Seldinger needle) through the abdominal wall and into the stomach. The needle is then removed while keeping the cannula in place. Next, a snare is inserted into the stomach via the endoscope and is looped over the distal end of the cannula. A first end of a flexible guidewire is then passed through the cannula and into the stomach where it is grasped by the snare, the second end of the guidewire remaining external to the patient. The endoscope and the snare are then withdrawn from the mouth of the patient to deliver the first end of the guidewire.

A push-type catheter implanting assembly is then inserted over the first end of the guidewire and is pushed over the guidewire towards its second end. The push-type catheter implanting assembly typically comprises a gastrostomy feeding tube, the gastrostomy feeding tube having a dome-shaped internal bolster disposed at its trailing end and having a tubular dilator serially connected to its leading end. The gastrostomy feeding tube and the internal bolster are typically made of a soft, biocompatible material, like silicone rubber, and may form a unitary structure. The dilator, which tapers in outer diameter from its trailing end to its leading end, is typically made of polyethylene or a like material which is stiffer than silicone but which still possesses some flexibility. Advancement of the push-type catheter implanting assembly over the guidewire continues until the front end of the dilator reaches the cannula and pushes the cannula out through the abdominal wall of the patient. The front end of the dilator is then pulled through the abdominal wall until the front or proximal end of the gastrostomy feeding tube emerges from the abdomen and, soon thereafter, the internal bolster at the rear or distal end of the gastrostomy feeding tube engages the gastric wall.

According to the pull method, the distal end of an endoscope is inserted into a patient's mouth and is passed through the esophagus into the stomach. After distension of the stomach by inflation, an entry site on the abdomen is identified, and an incision is made by passing a needle with an outer cannula (e.g., a Seldinger needle) through the abdominal wall and into the stomach. The needle is then removed while keeping the cannula in place. Next, a snare is inserted into the stomach via the endoscope and is looped over the distal end of the cannula. A first end of a suture is then passed through the cannula and into the stomach where it is grasped by the snare, the second end of the suture remaining external to the patient. The endoscope and the snare are then withdrawn from the mouth of the patient to deliver the first end of the suture. The first end of the suture is then coupled to the leading end of a pull-type catheter implanting assembly, the pull-type catheter implanting assembly comprising a gastrostomy feeding tube having an internal bolster at its trailing end and a plastic fitting at its leading end. The plastic fitting has a barbed rear portion mounted within the leading end of the feeding tube and a conical front portion that serves as a dilator, said conical front portion tapering in diameter from the leading end of the feeding tube to a front tip. A wire loop is fixed to the front tip of the plastic fitting, the first end of the suture being tied to the wire loop. Using the second end of the suture, the pull-type catheter implanting assembly is then pulled retrograde through the patient until the front or proximal end of the gastrostomy feeding tube emerges from the abdomen of the patient and, soon thereafter, the internal bolster at the rear or distal end of the gastrostomy feeding tube engages the gastric wall of the patient.

Regardless of whether the push method or the pull method is employed, the next steps of the procedure typically involve cutting and removing a proximal portion of the implanted gastrostomy feeding tube to reduce the externally-extending portion of the tube to a desired length (typically about 4-6 inches), securing an external bolster to the remaining exposed length of the implanted tube to prevent the withdrawal of the proximal end of the tube into the patient's stomach, and attaching a "Y-port" adaptor to the proximal end of the implanted feeding tube.

The Y-port adaptor is typically a unitary, tubular member made of silicone or the like and having an unbranched distal end and a branched proximal end. The unbranched distal end of the Y-port adaptor is typically shaped to include a barb, said barb being inserted into the proximal end of the implanted feeding tube and being appropriately sized to secure the Y-port adaptor to the feeding tube. The branched proximal end of the Y-port adaptor is typically shaped to include a pair of lumens, a larger diameter lumen and a smaller diameter lumen. The larger diameter lumen is adapted to receive the dispensing tip of a syringe or feeding set adapter of the type through which food is typically dispensed. The smaller diameter lumen is adapted to receive the dispensing tip of a syringe or feeding set adapter of the type through which medication is typically dispensed.

The Y-port adaptor typically also includes a pair of tethered plugs, the plugs being used to 'cap' the lumens when the lumens are not in use (the Y-port adaptor typically remaining secured at all times to the proximal end of the feeding tube). In this manner, the plugs prevent undesired materials from entering the patient through the Y-port adaptor. At the same time, the plugs are also intended to prevent the escape of the patient's stomach contents through the Y-port adaptor. As can readily be appreciated, the escape of the patient's stomach contents through the Y-port adaptor is undesirable as it often results in the soiling of the patient and/or his environment, thereby requiring cleanup. In addition, the escape of the patient's stomach contents may result in a loss of nutritional requirements to the patient. Furthermore, when the patient's stomach contents include contagions, the escape of the patient's stomach contents may result in the spread of disease to other individuals coming into contact with said stomach contents.

Unfortunately, the plugs used to cap the lumens of the Y-port adaptor have a tendency, over time and after repeated usage, to leak and to become easily ousted from their respective lumens. Moreover, for certain patients that suffer from conditions that result in increased stomach pressure (such as those suffering from Gastroparesis), it is not uncommon for the plugs to be expelled from their respective lumens simply by pressure exerted from within the stomach. As can readily be appreciated, the failure of the plugs to maintain a tight seal within their respective lumens leads to the undesirable escape of stomach contents through the Y-port adaptor.

Moreover, even if the plugs operate as desired to keep the lumens closed between feedings, one must still remove a plug from its respective lumen if one wishes to insert the dispensing tip of a syringe or feeding set adapter into the lumen so that food or medications may be administered to the patient. However, this temporary "opening" of the Y-port adaptor—subsequent to the removal of the plug and prior to the insertion of the dispensing tip into the lumen—presents an unfortunately ideal opportunity for the patient's stomach contents to be expelled from the patient. Moreover, because the removal of a plug is often performed by a healthcare provider standing directly in front of the Y-port adaptor, it is not uncommon for the healthcare provider, upon removing the plug from its lumen, to be sprayed with the patient's stomach contents, thereby subjecting the healthcare provider to any contagions present in the stomach contents.

SUMMARY OF THE INVENTION

It is an object of the present invention to provide a novel Y-port adaptor of the type suitable for use with medical catheters.

It is another object of the present invention to provide a Y-port adaptor as described above that overcomes at least some of the problems described above in connection with existing Y-port adaptors.

Therefore, according to one aspect of the invention, there is provided a Y-port adaptor suitable for use with a medical catheter, said Y-port adaptor comprising (a) a first arm, said first arm having a first end adapted for coupling to a medical catheter and defining a first lumen extending from said first end; (b) a second arm, said second arm having a second end and defining a second lumen extending from said second end, said second lumen being in fluid communication with said first lumen; (c) a third arm, said third arm having a third end and defining a third lumen extending from said third end, said third lumen being in fluid communication with said first lumen; and (d) valve means for controlling the flow of fluid between said first end and said second and third ends.

According to a first embodiment, the aforementioned valve means comprises a first valve and a second valve, said first valve being disposed within said second lumen to control the flow of fluid between said first end and said second end, said second valve being disposed within said third lumen to control the flow of fluid between said first end and said third end. Preferably, each of said first and second valves is an anti-reflux valve, such as a duckbill valve, said first anti-reflux valve being spaced inwardly from said second end by an appropriate distance to permit its being urged open by the insertion of a dispensing tip of a fluid dispensing device into said second lumen through said second end, said second anti-reflux valve being spaced inwardly from said third end by an appropriate distance to permit its being urged open by the insertion of a dispensing tip of a fluid dispensing device into said third lumen through said third end.

According to a second embodiment, the valve means comprises an anti-reflux valve, such as a duckbill valve, disposed within said first lumen, said anti-reflux valve permitting fluid to flow from said second lumen to said first end and from said third lumen to said first end but not from said first end to said second and third lumens.

According to a third embodiment, the valve means comprises a stopcock valve disposed within said first lumen, said stopcock valve having a first position in which fluid is permitted to flow between said second lumen and said first end and between said third lumen and said first end and a second position in which fluid is not permitted to flow between said second lumen and said first end and between said third lumen and said first end.

The Y-port adaptor of the present invention may be of the type wherein the second lumen is used to receive food and the third lumen is used to receive medications, the diameter of said second lumen preferably being greater than the diameter of said third lumen. In addition, the Y-port adaptor of the present invention preferably further comprises a first plug removably insertable into said second lumen through said second end, a second plug removably insertable into said third lumen through said third end, a first strap tethering said first plug to said second arm and a second strap tethering said second plug to said third arm.

The present invention is also directed to a medical catheter assembly, said medical catheter assembly including the Y-port adaptor described above and a medical catheter, said medical catheter having a proximal end, a distal end and a longitudinal conduit, the Y-port adaptor being coupled to the proximal end of the medical catheter. Preferably, said medical catheter is a PEG tube or a PEJ tube, said medical catheter assembly further comprising an internal bolster and an external bolster, said internal bolster being disposed at said distal end of said medical catheter, said external bolster being secured to said medical catheter at a point that is adapted to engage the patient externally. If desired, said internal bolster and said medical catheter may be integrally formed as a unitary structure.

For purposes of the present specification and claims, various relational terms like "top," "bottom," "proximal," "distal," "upper," "lower," "front," and "rear" are used to describe the present invention when said invention is positioned in or viewed from a given orientation. It is to be understood that, by altering the orientation of the invention, certain relational terms may need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

Figure 1:
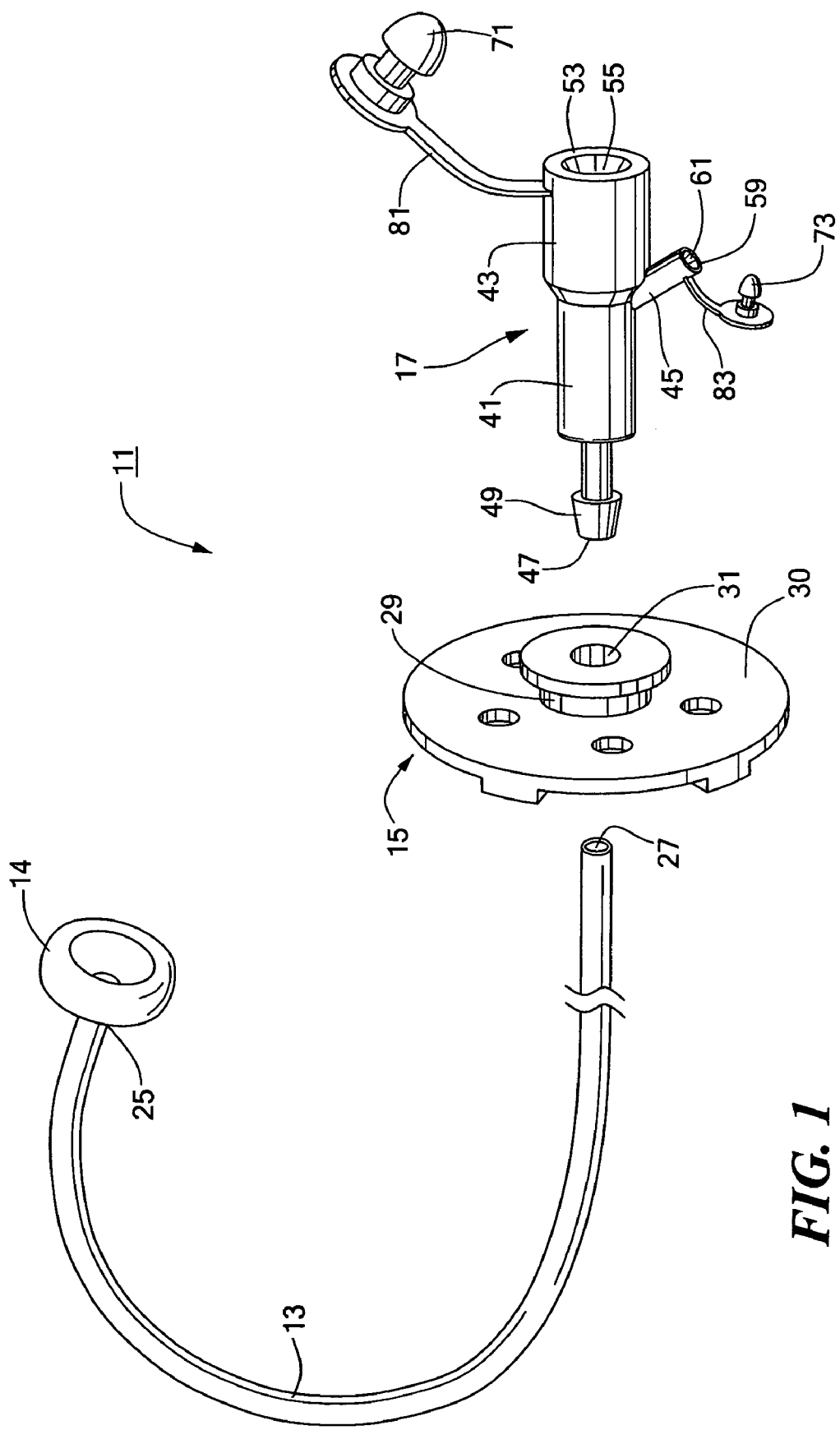
FIG. 1 is a fragmentary, exploded, perspective view of a first embodiment of a medical catheter assembly constructed according to the teachings of the present invention.
Figure 2:
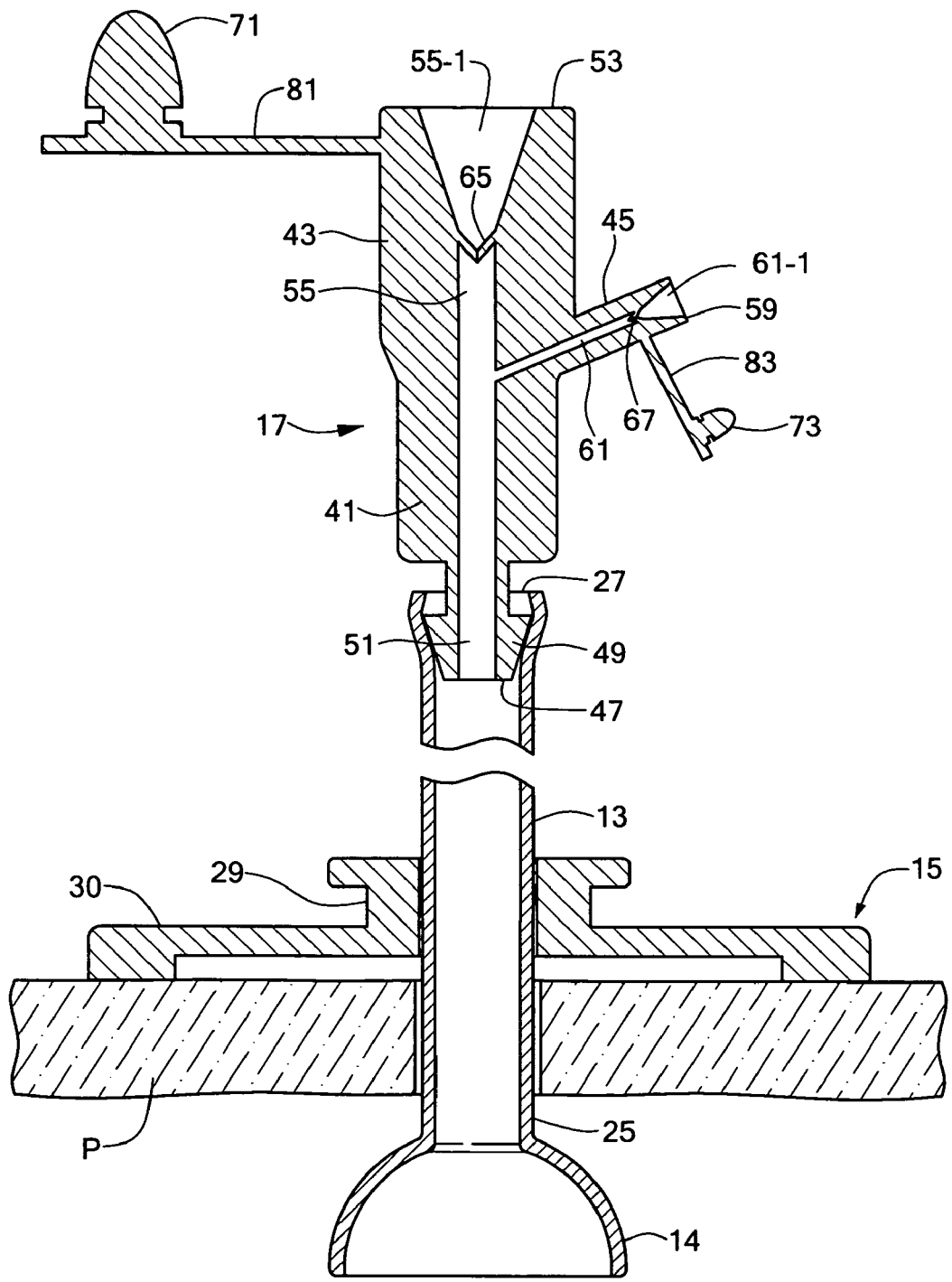
FIG. 2 is an enlarged, fragmentary, section view of the medical catheter assembly shown in FIG. 1, the medical catheter assembly being shown implanted in a patient.

Referring now to FIGS. 1 and 2, there are shown fragmentary, exploded, perspective and enlarged, fragmentary, section views, respectively, of a medical catheter assembly constructed according to the teachings of the present invention, said medical catheter assembly being represented generally by reference numeral 11. (It may be noted that, in FIG. 2, medical catheter assembly 11 is shown implanted in a patient P.)

Assembly 11 comprises a gastrostomy (or jejunostomy) feeding tube 13, an internal bolster 14, an external bolster 15, and a Y-port adaptor 17.

Tube 13, which may be a conventional gastrostomy (or jejunostomy) feeding tube, is an elongated, tubular member preferably made of a soft, biocompatible, silicone rubber. Tube 13 has a distal end 25 and a proximal end 27. A series of ruler markings (not shown) are printed on tube 13 and extend several inches from distal end 25 in the direction of proximal end 27 to facilitate the cutting of tube 13 to a desired length (after tube 13 has been implanted in a patient and before Y-port adaptor 17 is secured thereto).

Internal bolster 14, which is also made of a soft, biocompatible, silicone rubber, is an enlarged dome-shaped member securely disposed at distal end 25 of tube 13 for use in anchoring distal end 25 of tube 13 within a patient. In the present embodiment, bolster 14 forms a unitary structure with tube 13. As can readily be appreciated, bolster 14 may be modified to come in a variety of different shapes and sizes and may be replaced with a balloon-type bolster that is transformable between an expanded anchoring state and a collapsed state.

External bolster 15, which may be conventional, is a unitary member made of a biocompatible material, bolster 15 shaped to include an inner sleeve 29 and an outer annulus 30. Inner sleeve 29 is shaped to include a bore 31. Annulus 30 is adapted to lie against the skin of a patient in the area surrounding a feeding tract or stoma, with bore 31 being appropriately dimensioned to snugly receive therethrough the externally-extending portion of tube 13. In this manner, bolster 15 serves to keep the proximal end 27 of tube 13 from being withdrawn into the patient.

Y-port adaptor 17, which is a generally tubular member preferably made of silicone rubber or the like, comprises (i) an unbranched distal portion, i.e., a first arm 41, and (ii) a branched proximal portion, i.e., second and third arms 43 and 45, respectively. Arms 41, 43 and 45 are preferably integrally formed to provide a unitary structure. First arm 41 has a distal end 47, which is dimensioned for insertion into proximal end 27 of tube 13, distal end 47 being shaped to include a barb 49 for securing adaptor 17 to tube 13. A lumen 51 extends longitudinally through arm 41 and is accessible at distal end 47.

Second arm 43, which is substantially coaxial with first arm 41, is shaped to include a proximal end 53 and a lumen 55, lumen 55 extending longitudinally through arm 43 and being accessible at proximal end 53. A proximal portion 55-1 of lumen 55 is appropriately shaped and dimensioned to snugly receive the dispensing tip of a syringe or feeding set adaptor, and lumen 55 of second arm 43 and lumen 51 of arm 41 are appropriately arranged so as to be in fluid communication with one another.

Third arm 45, which lies off-axis with first arm 41, is shaped to include a proximal end 59 and a lumen 61, lumen 61 extending longitudinally through arm 45 and being accessible at proximal end 59. A proximal portion 61-1 of lumen 61 is appropriately shaped and dimensioned to snugly receive the dispensing tip of a syringe or feeding set adaptor, and lumen 61 of third arm 45 and lumen 51 of arm 41 are appropriately arranged so as to be in fluid communication with one another.

In the present embodiment, second arm 43 and its lumen 55 are greater in size than are third arm 45 and its lumen 61, respectively. This is because lumen 55 is intended to receive food, which is typically dispensed in comparatively larger fluid volumes, whereas lumen 61 is intended to receive medications, which are typically dispensed in comparatively smaller fluid volumes. Notwithstanding the above, it can readily be appreciated that the sizes of second arm 43 and its lumen 55 could be made to be identical to the sizes of third arm 45 and its lumen 61, respectively.

Y-port adaptor 17 further includes a first anti-reflux valve 65 and a second anti-reflux valve 67, first anti-reflux valve 65 being disposed within lumen 55 of second arm 43 and second anti-reflux valve 67 being disposed within lumen 61 of third arm 45. Anti-reflux valves 65 and 67 are preferably integrally formed with arms 43 and 45, respectively, to provide a unitary structure. Preferably, first anti-reflux valve 65 is appropriately positioned within lumen 55 so that it may be urged open by the insertion of the dispensing tip of a syringe or feeding set adapter into proximal portion 55-1 of lumen 55 but, in the absence of said dispensing tip, is biased shut. Similarly, second anti-reflux valve 67 is preferably positioned within lumen 61 so that it may be urged open by the insertion of the dispensing tip of a syringe or feeding set adapter into proximal portion 61-1 of lumen 61 but, in the absence of said dispensing tip, is biased shut. In this manner, anti-reflux valves 65 and 67 are opened only during the administration of food and/or medications to the patient. Between such administrations of food and/or medications, anti-reflux valves 65 and 67 are biased shut, thereby preventing the stomach contents of the patient from being expelled through lumens 55 and 61, respectively.

It should be noted that, although anti-reflux valves 65 and 67 are preferably positioned so that they are urged open by the insertion therethrough of a dispensing tip of a syringe or feeding set adapter, anti-reflux valves 65 and 67 may be positioned within lumens 55 and 61, respectively, further downstream of an inserted dispensing tip so that they are opened merely by the flow of fluid dispensed from the dispensing tip. However, one disadvantage with such an arrangement is that a sufficiently large fluid force from the dispensing tip needs to be provided to cause the valves to be opened. To generate such a force, however, may require unhealthy amounts of fluid pressure to be applied to the intestinal tract.

It should also be noted that, although first and second anti-reflux valves 65 and 67 are shown in the present embodiment as conventional duckbill valves, it can readily be appreciated that other types of anti-reflux valves could be used, such as ball-check valves, flapper valves, etc.

Y-port adaptor 17 further comprises a pair of plugs 71 and 73. Plug 71, which may be conventional in nature, is removably insertable into proximal portion 55-1 of lumen 55 so as to cap lumen 55 in a sealing fashion. Plug 73, which may be conventional in nature, is removably insertable into proximal portion 61-1 of lumen 61 so as to cap lumen 61 in a sealing fashion. Plug 71 is tethered to arm 43 by a flexible strap 81, and plug 73 is tethered to arm 45 by a flexible strap 83. Preferably, plug 71 and strap 81 form a unitary structure with arm 43, and plug 73 and strap 83 form a unitary structure with arm 45.

Figure 3:
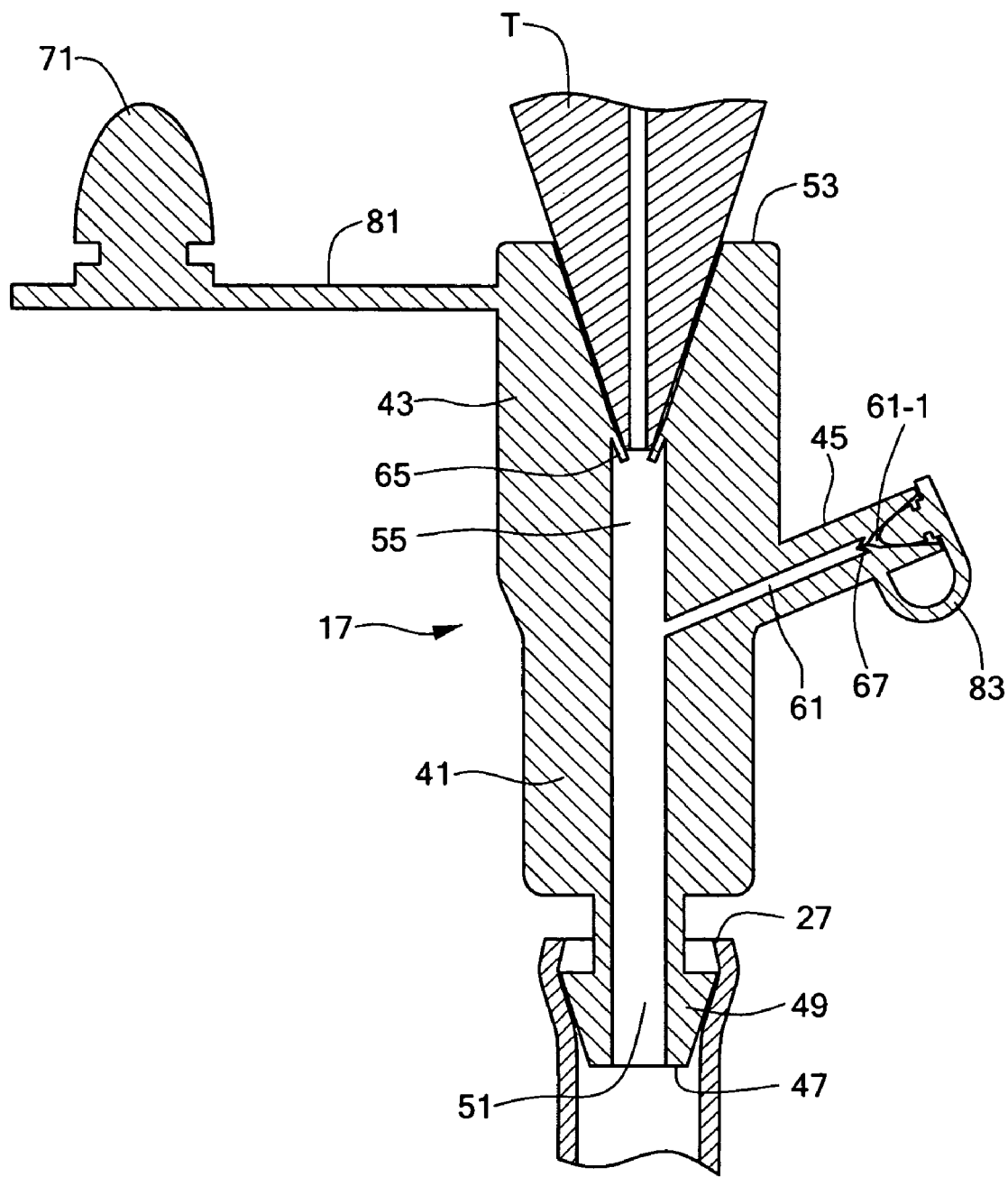
FIG. 3 is an enlarged, fragmentary, section view of the medical catheter assembly shown in FIG. 1, with the dispensing tip of a syringe or feeding set adapter inserted into one of the two input arms of the Y-port adaptor.

Medical catheter assembly 11 may be installed in a patient in the conventional manner (e.g., by implanting tube 13 and bolster 14 in the patient using percutaneous endoscopic gastrostomy or percutaneous endoscopic jejunostomy, by inserting external bolster 15 over the externally-extending portion of tube 13, by cutting tube 13 to a desired length, and by securing Y-port adaptor 17 to proximal end 27 of tube 13). With assembly 11 thus installed, food may be administered to the patient by removing plug 71 from lumen 55, by inserting the dispensing tip T of a syringe or a feeding set adapter into proximal portion 55-1 of lumen 55 to open valve 63 (see FIG. 3) and then by dispensing the food through the dispensing tip into lumen 55 past valve 63. Medications may be administered to the patient simultaneously with or alternatively to the aforementioned administration of food by removing plug 73 from lumen 61, by inserting the dispensing tip of a syringe or feeding set adapter into proximal portion 61-1 of lumen 61 to open valve 67, and then by dispensing the medications through the dispensing tip into lumen 61 past valve 67. (It should be understood that, although lumen 55 is described above as being adapted to receive food and lumen 61 is described above as being adapted to receive medications, lumen 55 may alternatively be used to receive medications and lumen 61 may alternatively be used to receive food.) As can be seen, one benefit of assembly 11, as compared to comparable conventional assemblies, is that plugs 71 and 73 need not be relied upon to prevent the expulsion of the patient's stomach contents through Y-port adaptor 17 as this duty is already being ably performed by valves 65 and 67. In fact, even when plugs 71 and 73 are removed from lumens 55 and 61, respectively (e.g., to permit the insertion of a dispensing tip into a desired lumen), valves 65 and 67 prevent the expulsion of the patient's stomach contents through Y-port adaptor 17.

Another benefit of assembly 11, as compared to comparable conventional assemblies, is that, if desired, one may relieve excessive gastric pressure in a patient in a more controlled manner than is presently feasible. As can readily be appreciated, excessive gastric pressure can be uncomfortable and/or dangerous to a patient. At present, excessive gastric pressure in a patient is typically relieved by slowly and carefully removing the plug of a Y-port adaptor from its corresponding lumen, thereby allowing gas to escape through the unplugged lumen. However, such a technique (often called "decompression") may also result in the uncontrolled release of stomach solids and liquids through the unplugged lumen. By contrast, assembly 11 permits a healthcare provider to perform decompression by inserting into an unplugged lumen a hollow tip coupled to an evacuation tube. The hollow tip urges open the anti-reflux valve in the unplugged lumen and the evacuation tube conducts any liquids or solids expelled through the thus-opened lumen into a desired receptacle.

Figure 4:
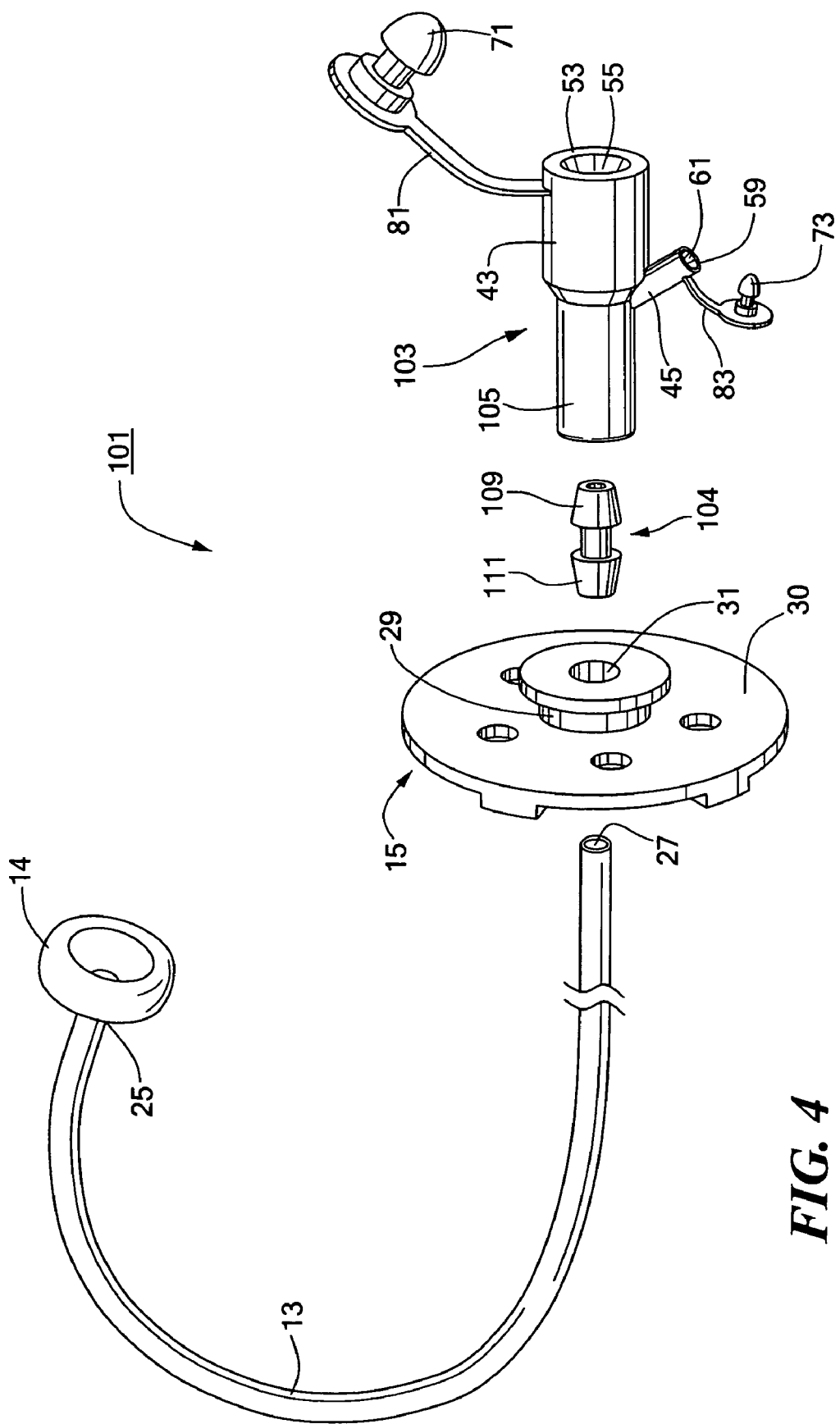
FIG. 4 is a fragmentary, exploded, perspective view of a second embodiment of a medical catheter assembly constructed according to the teachings of the present invention.
Figure 5:
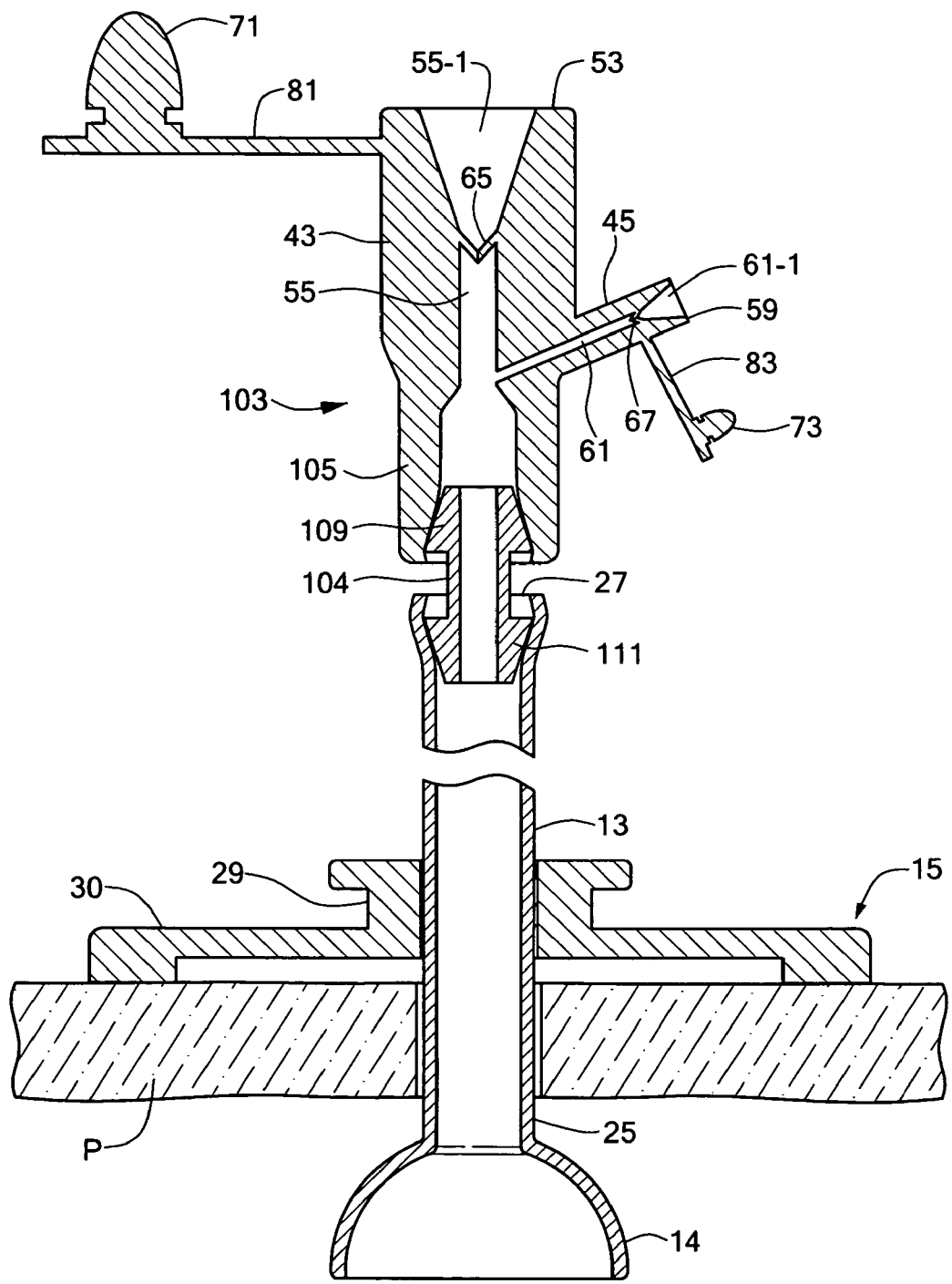
FIG. 5 is an enlarged, fragmentary, section view of the medical catheter assembly shown in FIG. 4, the medical catheter assembly being shown implanted in a patient.

Referring now to FIGS. 4 and 5, there are shown fragmentary, exploded, perspective and enlarged, fragmentary section views, respectively, of a second embodiment of a medical catheter assembly constructed according to the teachings of the present invention, said medical catheter assembly being represented generally by reference numeral 101. (It may be noted that, in FIG. 5, medical catheter assembly 101 is shown implanted in a patient.)

Assembly 101 is similar in many respects to assembly 11, the principal difference between the two assemblies being that, in assembly 101, Y-port adaptor 17 of assembly 11 is replaced with the combination of a Y-port adaptor 103 and a tubular connector 104.

Y-port adaptor 103 is similar in most respects to Y-port adaptor 17, the primary difference between the two Y-port adaptors being that Y-port adaptor 103 has a first arm 105 that does not include a barb at its distal end 107. Consequently, Y-port adaptor 107 is not connected directly tube 13. Instead, tubular connector 104 has a barb-shaped proximal end 109 and a barb-shaped distal end 111, proximal end 109 of connector 104 being inserted into distal end 107 of first arm 105 to couple Y-port adaptor 17 to connector 104, distal end 111 of connector 104 being inserted into proximal end 27 of tube 13 to couple connector 104 to tube 13.

Assembly 101 is implanted in a patient in essentially the same manner as is assembly 11, the only difference being that, as noted above, Y-port adaptor 103 is not attached directly to tube 13, but rather, is indirectly connected to tube 13 through connector 104. Once implanted in a patient, assembly 101 is used in the same fashion as assembly 11.

Figure 6:
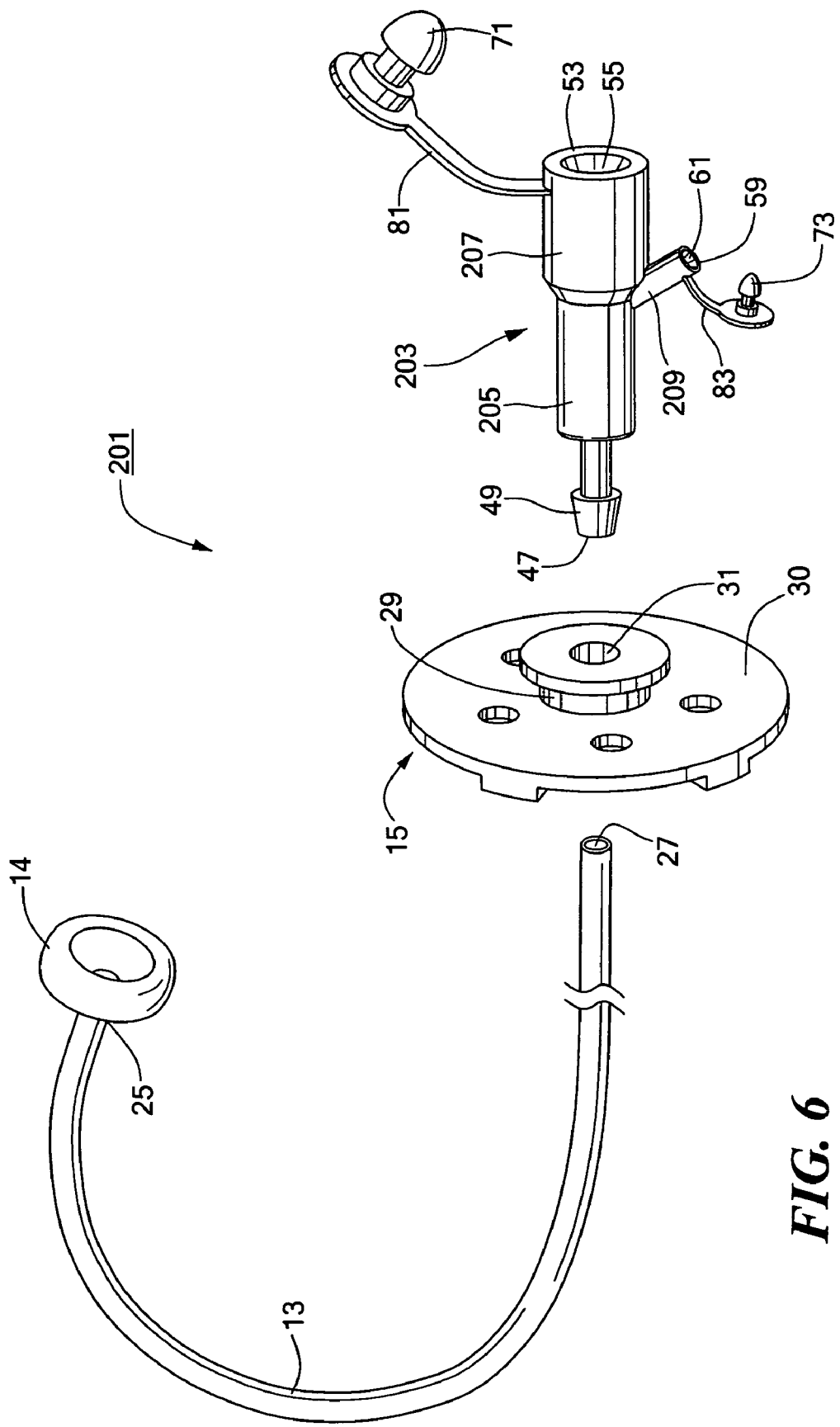
FIG. 6 is a fragmentary, exploded, perspective view of a third embodiment of a medical catheter assembly constructed according to the teachings of the present invention.
Figure 7:
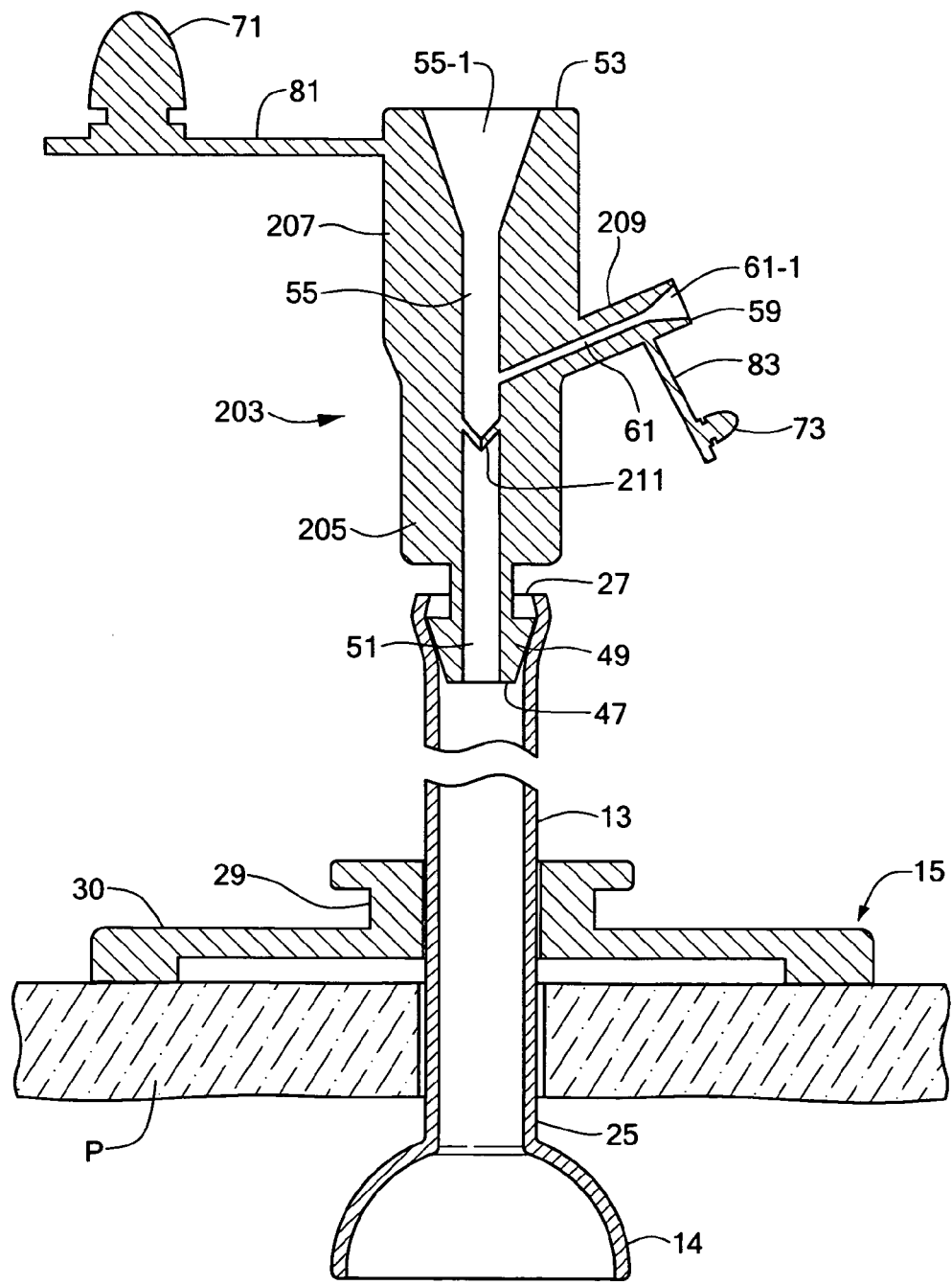
FIG. 7 is an enlarged, fragmentary, section view of the medical catheter assembly shown in FIG. 6, the medical catheter assembly being shown implanted in a patient.

Referring now to FIGS. 6 and 7, there are shown fragmentary, exploded, perspective and enlarged, fragmentary, section views, respectively, of a third embodiment of a medical catheter assembly constructed according to the teachings of the present invention, said medical catheter assembly being represented generally by reference numeral 201. (It may be noted that, in FIG. 7, medical catheter assembly 201 is shown implanted in a patient.)

Assembly 201 is similar in most respects to assembly 11, the principal difference between the two assemblies being that assembly 201 includes a Y-port adaptor 203, instead of Y-port adaptor 17.

Y-port adaptor 203, which is similar in most respects to Y-port adaptor 17, has first, second and third arms 205, 207 and 209 that correspond to first, second and third arms 41, 43 and 45, respectively, of adaptor 17. The primary difference between the two Y-port adaptors is that Y-port adaptor 203 does not include first and second anti-reflux valves 65 and 67 disposed within its second and third arms 207 and 209, respectively. Instead, Y-port adaptor 203 includes a single anti-reflux valve 211 disposed within its first arm 205. Valve 211, which is preferably integrally formed with arm 205 to provide a unitary structure, is shown in the present embodiment as a duckbill valve but may be any type of anti-reflex valve, such as a ball-check valve, a flapper valve, etc.

Figure 8:
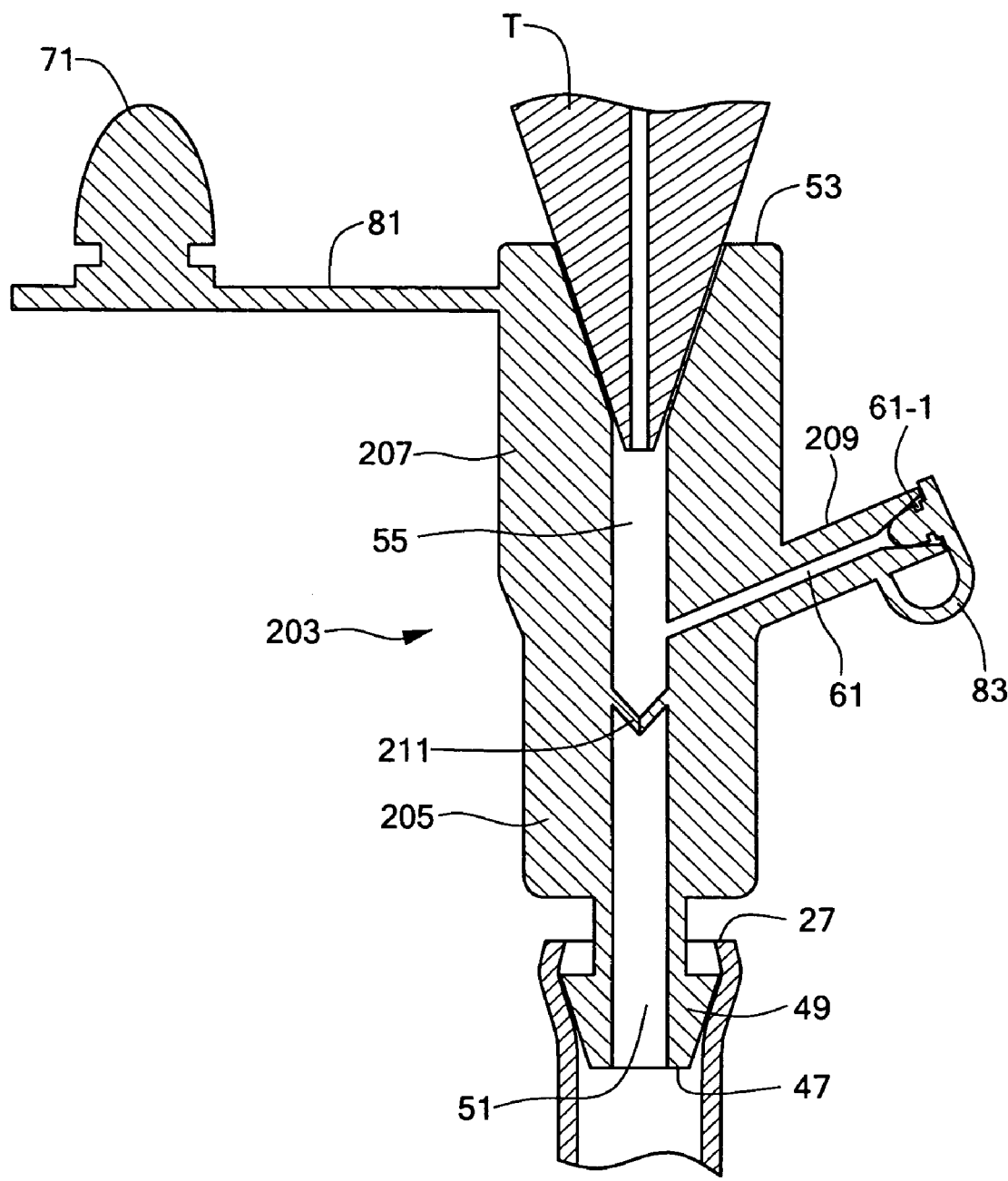
FIG. 8 is an enlarged, fragmentary, section view of the medical catheter assembly shown in FIG. 6, with the dispensing tip of a syringe or feeding set adapter inserted into one of the two input arms of the Y-port adaptor.

Assembly 201 is implanted in a patient in the same manner as is assembly 11. Once implanted, assembly 201 is used in much the same way as assembly 11, with one exception. Because valve 211 is located within first arm 205, instead of being located within second arm 207 or third arm 209, valve 211 cannot be urged open by inserting a dispensing tip of a syringe or feeding set adapter into second arm 207 or third arm 209 (see FIG. 8). Instead, valve 211 must be urged open by the flow of fluid dispensed from the dispensing tip or by a yet-to-be-designed dispensing tip. As noted above, one potential disadvantage to using the flow of fluid to urge open such a valve is that the fluid force necessary to cause the valve to be opened would likely be so great as to require an unhealthy amount of fluid pressure to be applied to the intestinal tract. Another disadvantage to using a single valve (as in Y-port adaptor 203), as compared to a pair of valves (as in Y-port adaptor 17 or Y-port adaptor 103), is that the opening of said single valve results in all of the ports being open at the same time, thereby making it possible for fluid backflow to occur through one of the other ports.

Figure 9:
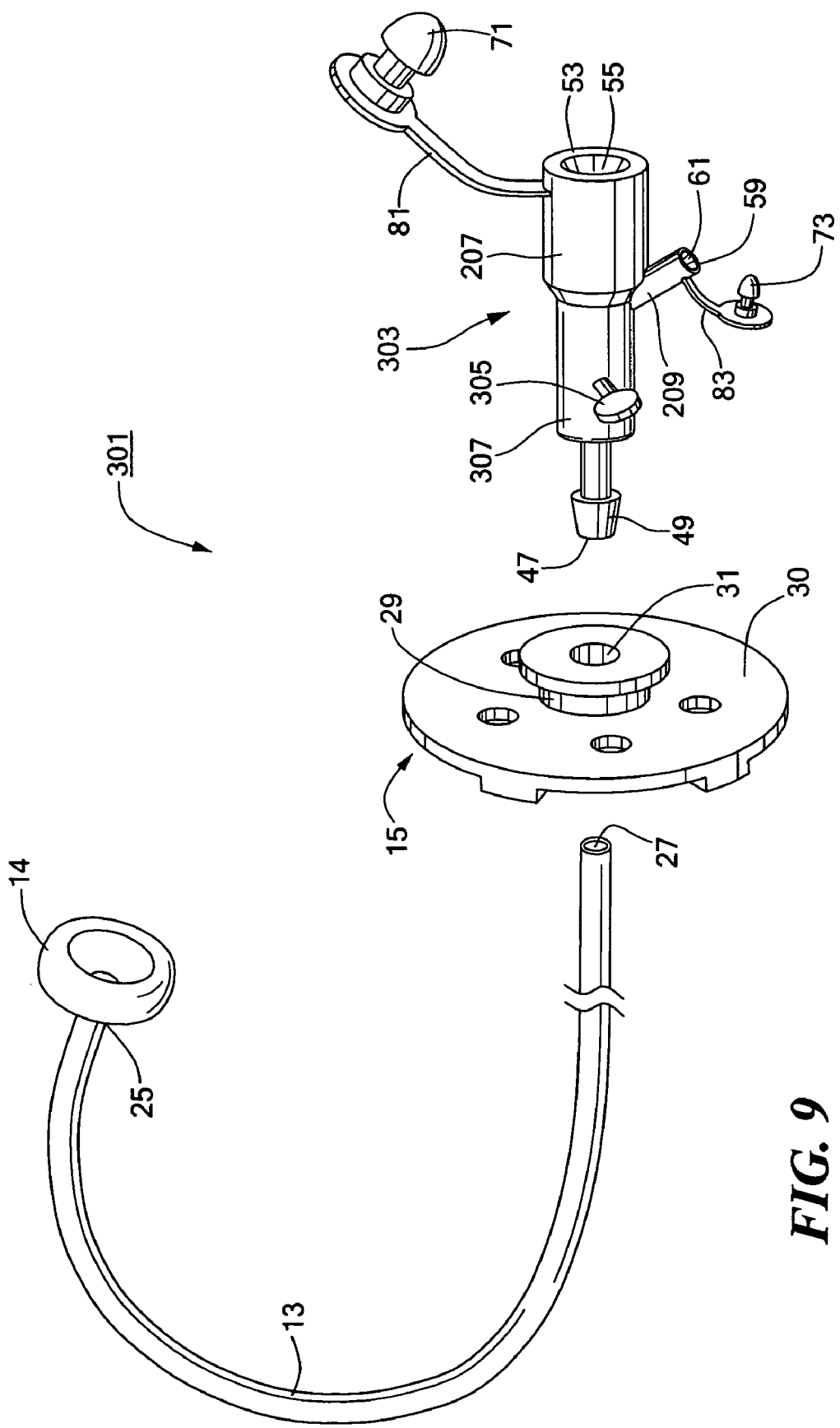
FIG. 9 is a fragmentary, exploded, perspective view of a fourth embodiment of a medical catheter assembly constructed according to the teachings of the present invention.
Figure 10:
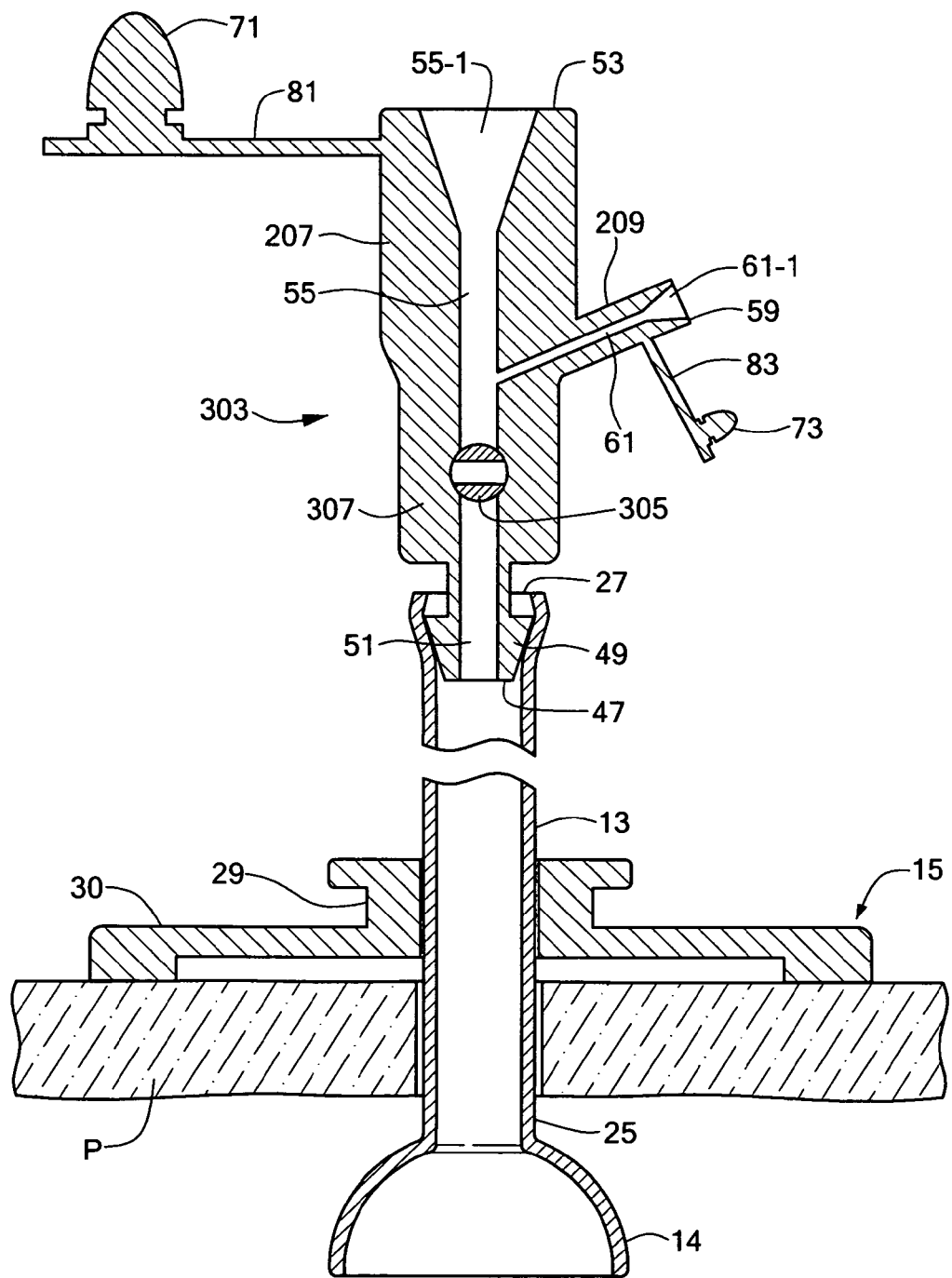
FIG. 10 is an enlarged, fragmentary, section view of the medical catheter assembly shown in FIG. 9, the medical catheter assembly being shown implanted in a patient.

Referring now to FIGS. 9 and 10, there are shown fragmentary, exploded, perspective and enlarged, fragmentary, section views, respectively, of a fourth embodiment of a medical catheter assembly constructed according to the teachings of the present invention, said medical catheter assembly being represented generally by reference numeral 301. (It may be noted that, in FIG. 10, medical catheter assembly 301 is shown implanted in a patient.) Assembly 301 is similar in most respects to assembly 201, the principal difference between the two assemblies being that assembly 301 includes a Y-port adaptor 303, instead of Y-port adaptor 201.

Y-port adaptor 303 is similar in most respects to Y-port adaptor 203, the primary difference between the two Y-port adaptors being that Y-port adaptor 303 does not include an anti-reflux valve 211, but rather, includes a stopcock valve 305 in its first arm 307.

Figure 11:
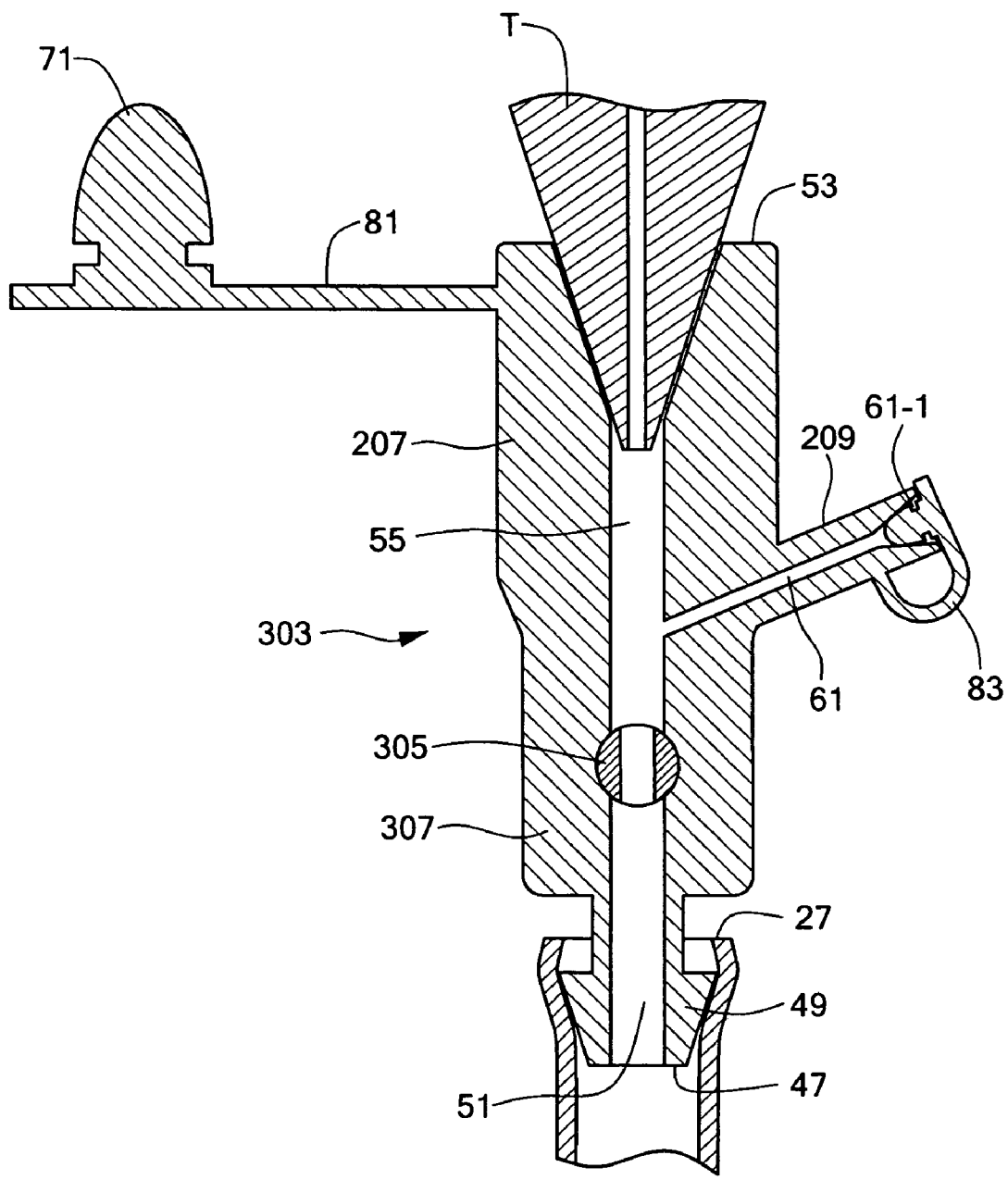
FIG. 11 is an enlarged, fragmentary, section view of the medical catheter assembly shown in FIG. 9, with the dispensing tip of a syringe or feeding set adapter inserted into one of the two input arms of the Y-port adaptor and the stopcock valve placed in its open position.
Figure 12:
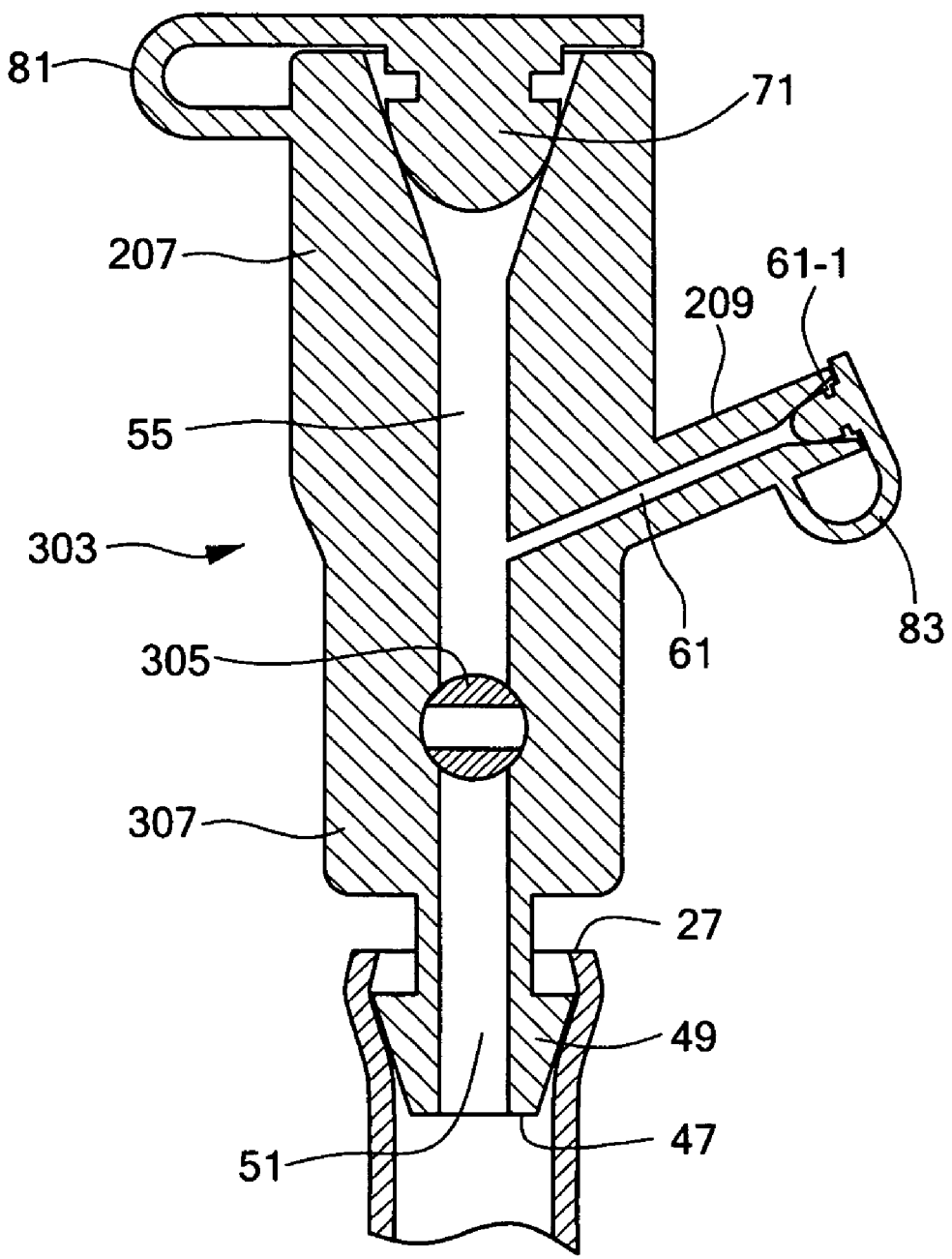
FIG. 12 is an enlarged, fragmentary, section view of the medical catheter assembly shown in FIG. 9, with the dispensing tip of a syringe or feeding set adapter inserted into one of the two input arms of the Y-port adaptor and the stopcock valve placed in its closed position.

Assembly 301 is implanted in a patient in the same manner as is assembly 201. Once implanted, assembly 301 is used in much the same way as assembly 201, with one exception. When one wishes to administer food and/or medications to the patient, one inserts the dispensing tip(s) into arms 207 and/or 209 and then turns stopcock valve 305 to its open position (see FIG. 11). Between feedings, stopcock valve 305 is turned to its closed position (see FIG. 12).

As compared to assemblies 11 and 101, assembly 301 also suffers from the disadvantage that the opening of stopcock valve 305 results in all of the ports being open at the same time, thereby making it possible for fluid backflow to occur through one of the other ports. In addition, as compared to assemblies 11 and 101 wherein the insertion of a dispensing tip automatically opens a desired valve, assembly 301 suffers from the disadvantage that an operator must actively change stopcock valve 305 between its open and closed positions.

Figure 13:
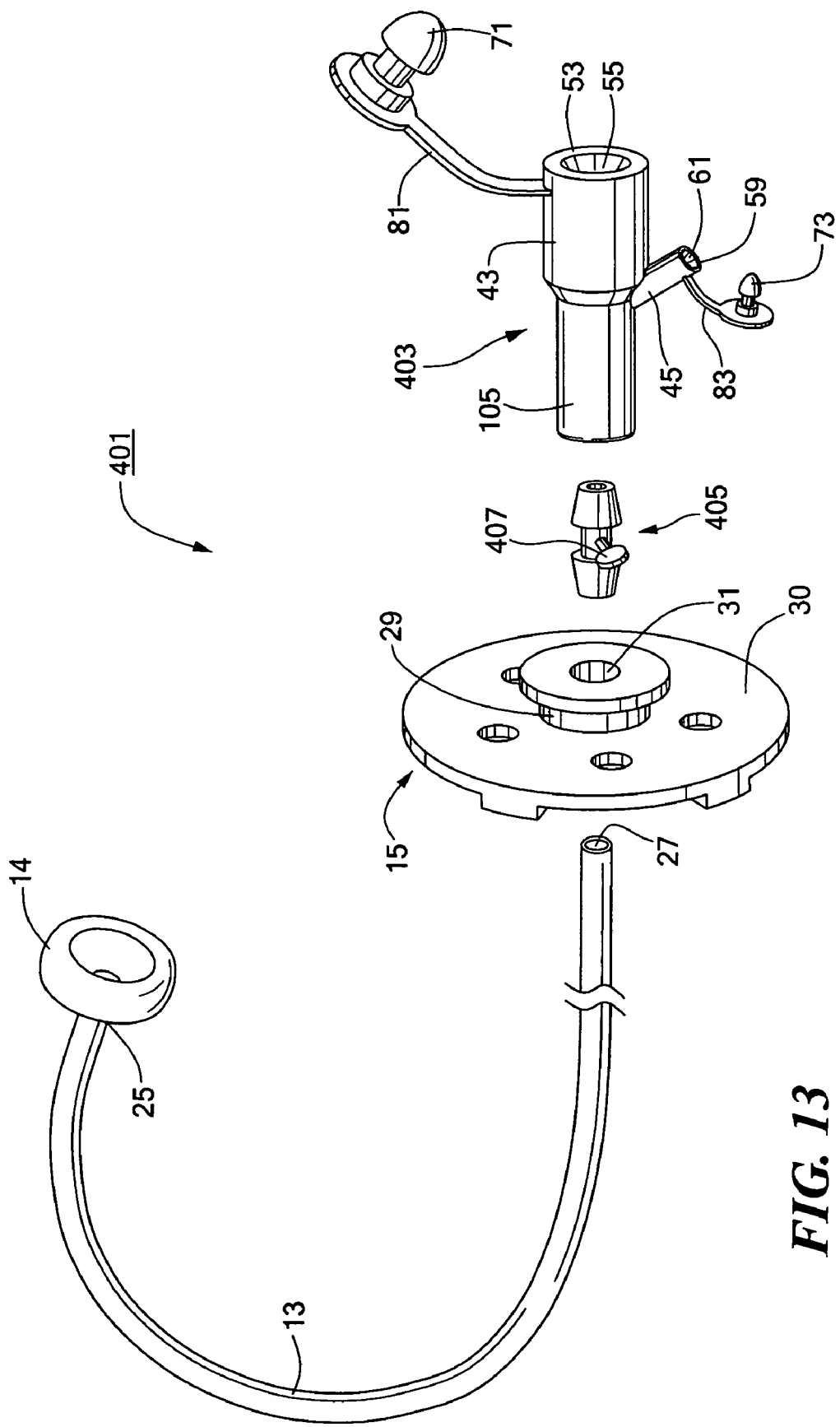
FIG. 13 is an enlarged, fragmentary, section view of a fifth embodiment of a medical catheter assembly constructed according to the teachings of the present invention.

Referring now to FIG. 13, there is shown an enlarged, fragmentary, section view of a fifth embodiment of a medical catheter assembly constructed according to the teachings of the present invention, said medical catheter assembly being represented generally by reference numeral 401.

Assembly 401 is similar in certain respects to assembly 101, the principal differences between the two assemblies being that assembly 401 includes a Y-port adaptor 403 and a tubular connector 405, instead of Y-port adaptor 103 and tubular connector 104 of assembly 101.

Y-port adaptor 403 is similar in many respects to Y-port adaptor 104, the principal difference between the two Y-port adaptors being that Y-port adaptor 403 does not include anti-reflux valves 65 and 67.

Connector 405 is similar in many respects to connector 403, the principal difference between the two connectors being that connector 405 additionally includes a stopcock valve 407.

Assembly 401 is implanted in a patient in the same type of manner as is assembly 101. Once implanted in a patient, assembly 401 is used in the same fashion as assembly 301.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A Y-port adaptor suitable for use with a medical catheter, said Y-port adaptor comprising:
   (a) a first arm, said first arm having a first end, said first end being shaped to include a barb for coupling said first arm to a medical catheter, said first arm defining a first lumen extending from said first end;
   (b) a second arm, said second arm having a second end and defining a second lumen extending from said second end, said second lumen being in fluid communication with said first lumen;
   (c) a third arm, said third arm having a third end and defining a third lumen extending from said third end, said third lumen being in fluid communication with said first lumen;
   (d) valve means for controlling the flow of fluid between said first end and said second and third ends, wherein said valve means comprises a first valve and a second valve, wherein the valves are biased in a closed position thereby preventing fluid flow therethrough, said first valve being integrally formed with the second arm and disposed within said second lumen to control the flow of fluid between said first end and said second end, said second valve being integrally formed with the third arm and disposed within said third lumen to control the flow of fluid between said first end and said third end, wherein the first valve is spaced from the second end and the second valve is spaced from the third end;
   (e) a first plug removably mounted on said second end of said second arm; and
   (f) a second plug removably mounted on said third end of said third arm;
   (g) wherein said Y-port adaptor is made of silicone and is formed as a unitary, one-piece structure.

2. The Y-port adaptor as claimed in claim 1 wherein said first valve comprises a first anti-reflux valve and wherein said second valve comprises a second anti-reflux valve, said first anti-reflux valve being disposed within said second lumen to prevent fluid flow therepast in a direction from said first end to said second end, said second anti-reflux valve being disposed within said third lumen to prevent fluid flow therepast in a direction from said first end to said third end.

3. The Y-port adaptor as claimed in claim 2 wherein each of said first and second anti-reflux valves is a duckbill valve.

4. The Y-port adaptor as claimed in claim 2 wherein said first anti-reflux valve is spaced within said second lumen a short distance from said second end and wherein said second anti-reflux valve is spaced within said third lumen a short distance from said third end.

5. The Y-port adaptor as claimed in claim 4 wherein said first anti-reflux valve is positioned within said second lumen in such a manner as to be urged open by insertion of a dispensing tip of a fluid dispensing device into said second lumen through said second end and wherein said second anti-reflux valve is positioned within said third lumen in such a manner as to be urged open by insertion of a dispensing tip of a fluid dispensing device into said third lumen through said third end.

6. The Y-port adaptor as claimed in claim 1 wherein each of said second lumen and said third lumen has a diameter and wherein the diameter of said second lumen is greater than the diameter of said third lumen.

7. The Y-port adaptor as claimed in claim 1 further comprising a first strap tethering said first plug to said second arm and a second strap tethering said second plug to said third arm.

8. The Y-port adaptor as claimed in claim 1 wherein said first valve and said second valve are independently operable.

9. A medical catheter assembly comprising:
   (a) a medical catheter, said medical catheter having a proximal end, a distal end and a longitudinal conduit;
   (b) a Y-port adaptor, said Y-port adaptor comprising
      (i) a first arm, said first arm having a first end shaped to include a barb and coupled to said proximal end of said medical catheter, said first arm defining a first lumen extending from said first end, said first lumen being in fluid communication with said longitudinal conduit of said medical catheter;
      (ii) a second arm, said second arm having a second end and defining a second lumen extending from said second end, said second lumen being in fluid communication with said first lumen;
      (iii) a third arm, said third arm having a third end and defining a third lumen extending from said third end, said third lumen being in fluid communication with said first lumen;
      (iv) valve means for controlling the flow of fluid between said first end and said second and third ends, wherein said valve means comprises a first valve and a second valve, said first valve being integrally formed with the second arm and disposed within said second lumen to control the flow of fluid between said first end and said second end, said second valve being integrally formed with the third arm and disposed within said third lumen to control the flow of fluid between said first end and said third end;
      (v) a first plug removably mounted on said second end of said second arm; and
      (vi) a second plug removably mounted on said third end of said third arm; and
   (c) a first fluid dispensing device, said first fluid dispensing device having a first fluid dispensing tip insertable into said second lumen through said second end;
   (d) wherein said first valve is positioned within said second lumen so that, when said first fluid dispensing tip is inserted into said second lumen, said first valve is urged open directly by said first fluid dispensing tip and so that, in the absence of said first fluid dispensing tip from said second lumen, said first valve is biased shut.

10. The medical catheter assembly as claimed in claim 9 wherein said medical catheter is one of a PEG tube and a PEJ tube, said medical catheter assembly further comprising an internal bolster disposed at said distal end of said medical catheter.

11. The medical catheter assembly as claimed in claim 10 wherein said internal bolster and said medical catheter are integrally formed as a unitary structure.

12. The medical catheter assembly as claimed in claim 10 further comprising an external bolster secured to said medical catheter.

13. The medical catheter assembly as claimed in claim 9 further comprising a second fluid dispensing device, said second fluid dispensing device having a fluid dispensing tip insertable into said third lumen through said third end and wherein said second valve is positioned within said third lumen so that, when said fluid dispensing tip of said second fluid dispensing device is inserted into said third lumen, said second valve is urged open by said fluid dispensing tip of said second fluid dispensing device and so that, in the absence of said fluid dispensing tip of said second fluid dispensing device from said third lumen, said second valve is biased shut.

14. The medical catheter assembly as claimed in claim 13 wherein said first valve comprises a first anti-reflux valve and wherein said second valve comprises a second anti-reflux valve, said first anti-reflux valve being disposed within said second lumen to prevent fluid flow therepast in a direction from said first end to said second end, said second anti-reflux valve being disposed within said third lumen to prevent fluid flow therepast in a direction from said first end to said third end.

15. The medical catheter assembly as claimed in claim 14 wherein each of said first and second anti-reflux valves is a duckbill valve.

16. The medical catheter assembly as claimed in claim 9 wherein each of said second lumen and said third lumen has a diameter and wherein the diameter of said second lumen is greater than the diameter of said third lumen.

17. The medical catheter assembly as claimed in claim 9 further comprising a first strap tethering said first plug to said second arm and a second strap tethering said second plug to said third arm.

18. The medical catheter assembly as claimed in claim 9 wherein said Y-port adaptor is a one-piece structure made of silicone rubber.

19. The medical catheter assembly as claimed in claim 9 wherein said first valve and said second valve are independently operable.

20. A Y-port adaptor suitable for use with a medical catheter, said Y-port adaptor comprising:
(a) a first arm, said first arm having a first end, said first end being shaped to include a barb for coupling said first arm to a medical catheter, said first arm defining a first lumen extending from said first end;
(b) a second arm, said second arm having a second end and defining a second lumen extending from said second end, said second lumen being in fluid communication with said first lumen;
(c) a third arm, said third arm having a third end and defining a third lumen extending from said third end, said third lumen being in fluid communication with said first lumen;
(d) valve means for controlling the flow of fluid between said first end and said second and third ends, wherein said valve means comprises a first valve and a second valve, said first valve being integrally formed with the second arm and disposed within said second lumen to control the flow of fluid between said first end and said second end, said second valve being integrally formed with the third arm and disposed within said third lumen to control the flow of fluid between said first end and said third end, wherein each of said first valve and said second valve is an anti-reflux valve, wherein said first valve and said second valve are independently operable, and wherein the first valve is spaced away from the second end and the second valve is spaced away from the third end;
(e) a first plug removably mounted on said second end of said second arm; and
(f) a second plug removably mounted on said third end of said third arm;
(g) wherein said Y-port adaptor is a unitary, one-piece structure made of silicone.

21. The Y-port adaptor of claim 20 wherein said first valve is a duckbill valve and wherein said second valve is a duckbill valve.

* * * * *

UNITED STATES PATENT AND TRADEMARK OFFICE
CERTIFICATE OF CORRECTION

PATENT NO. : 7,628,775 B2  Page 1 of 1
APPLICATION NO. : 10/950026
DATED : December 8, 2009
INVENTOR(S) : Adams et al.

It is certified that error appears in the above-identified patent and that said Letters Patent is hereby corrected as shown below:

Title Page, Item (57) Abstract, line 10, "is fluid" should be changed to --is in fluid--;
Column 3, line 37, "patients that" should be changed to --patients who--;
Column 6, lines 10-12, "with the dispensing tip of a syringe or feeding set adapter inserted into one of the two input arms of the Y-port adaptor and the stopcock" should be changed to --with the stopcock--;
Column 8, line 24, "valve 63" should be changed to --valve 65--;
Column 8, line 26, "valve 63" should be changed to --valve 65--;
Column 9, line 16, "Y-port adaptor 107" should be changed to --Y-port adaptor 103--;
Column 9, line 16, "directly tube" should be changed to --directly to tube--;
Column 9, line 20, "Y-port adaptor 17" should be changed to --Y-port adaptor 103--;
Column 10, lines 17-18, "Y-port adaptor 201" should be changed to --Y-port adaptor 203--;
Column 10, line 53, "adaptor 104" should be changed to --adaptor 103--;
Column 10, lines 56-57, "connector 403" should be changed to --connector 104--; and
Column 10, line 63, "assembly 301" should be changed to --assembly 101--.

Signed and Sealed this

Thirteenth Day of July, 2010

David J. Kappos
*Director of the United States Patent and Trademark Office*

UNITED STATES PATENT AND TRADEMARK OFFICE
CERTIFICATE OF CORRECTION

PATENT NO.       : 7,628,775 B2                                          Page 1 of 1
APPLICATION NO.  : 10/950026
DATED            : December 8, 2009
INVENTOR(S)      : Adams et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 749 days.

Signed and Sealed this

Second Day of November, 2010

David J. Kappos
*Director of the United States Patent and Trademark Office*